US007344685B2

(12) United States Patent
McNulty

(10) Patent No.: US 7,344,685 B2
(45) Date of Patent: Mar. 18, 2008

(54) OZONIZER APPARATUS EMPLOYING A MULTI-COMPARTMENT BAG FOR STERILIZING

(76) Inventor: James F. McNulty, 1290 Third St., Calimesa, CA (US) 92320

( * ) Notice: Subject to any disclaimer, the term of this patent is extended or adjusted under 35 U.S.C. 154(b) by 813 days.

(21) Appl. No.: 10/761,038

(22) Filed: Jan. 17, 2004

(65) Prior Publication Data
US 2005/0158221 A1 Jul. 21, 2005

(51) Int. Cl.
B01J 19/08 (2006.01)
(52) U.S. Cl. .................... 422/186.07; 422/186.12; 422/292
(58) Field of Classification Search .......... 422/186.07, 422/186.12, 292
See application file for complete search history.

(56) References Cited
U.S. PATENT DOCUMENTS
6,007,770 A    12/1999  Peiper et al.
6,149,878 A *  11/2000  Jacob et al. ........... 422/186.04
6,365,103 B1 * 4/2002  Fournier ..................... 422/33

* cited by examiner

Primary Examiner—Kishor Mayekar
(74) Attorney, Agent, or Firm—Leonard Tachner

(57) ABSTRACT

A sealed multi-chambered bag, that is a flexible container, is made of dielectric material and contains two electrode plates (preferably screen plates) that are separated by an internal wall of the bag. Materials to be sterilized are placed between one or the other or both of the electrode plates and the interior wall. The interior wall allows the plates to be contained within the bag without the risk of damaging high voltage discharges occurring between plates optimal ozone production occurs in the bag immediately adjacent to where the materials to be sterilized are located. The bag is placed within a chamber containing an aperture which is connected to the intake of a pump. A conductor connects each electrode plate to an opposed terminal of a high tension transformer. Both the pump and the transformer are connected to timing circuitry, which turns on the pump and the transformer and, then periodically turns the pump off and on to deflate and re-inflate the chambered bag and circulates the ozone produced therein to all virulence on the materials being sterilized. The gas within the bag alternatively expands and compresses before the transformer is turned off. The timer circuit allows the pump to continue to cycle on and off thereafter (preferably at an increased cycling rate) until the ozone off gas remaining in the bag is destroyed by molecular collision, surface reactions or otherwise.

5 Claims, 2 Drawing Sheets

OZONIZER APPARATUS EMPLOYING A MULTI-COMPARTMENT BAG FOR STERILIZING

BACKGROUND OF THE INVENTION

Field of the Invention

To avoid the iatrogenic infection of patients, medical instruments, applications, garments and bedding are routinely sterilized prior to their use in treatment settings. An object is sterile when no viable population lives upon it. This is as opposed to sanitizing or disinfecting, which is normally accomplished with germicidal solutions or ozonators and which only requires the destruction of select populations of inoculum. The methods of sterilization commonly practiced are moist heat (autoclaves), dry heat (ovens) and ethylene oxide (ethylene oxide sterilizers) sterilization. All of these methods of sterilization are most problematic.

The methods take undesirable amounts of time to sterilize. With preparation and cooling or dissipation times included, these methods take from at least an hour to as long as several days to safely sterilize materials.

Destruction of the heat resistant B. stearothermopolis endospore is a gold standard for evaluating the effectiveness of sterilizers. If these endospores, the most heat resistant of all known microbes, are rendered inviable, then, it is assumed that all other bacteria and the much smaller viruses are also enviable. Heat at or above 250° F. will kill the B. stearothermopolis endospore.

Moist heat kills bacterial and viral cells by denaturing their proteins, that is by destroying the functional tertiary structure of the proteins. This requires time for the protein's polypeptide chains to be sufficiently agitated thermally to disturb the residual charges causing the chain to fold back upon itself. Moist heat at 250° F. takes about one-half hour to sterilize objects inoculated with the hardy B. stearothermopolis endospores. Steam with a temperature of at least 250° F. can be generated under pressure in an autoclave. After about 30 minutes, heat from the 250° F. pressurized steam will distribute to all inoculum on the autoclave's contents. The continuously generated moist heat distributes to the inoculum by forced convection and thermal conduction. With steam, this distribution is aided by condensation and release of the latent heat of vaporization. A complete autoclave cycle, from preparation with ultrasonic scaling to post treatment drying and cooling, typically takes 1 hour. Chemiclaves, which are hybrid autoclaves that heat germicidal liquids, are normally operated at even higher temperatures than autoclaves, and, therefore, there is a hazard of even greater heat damage to the worked contents.

Dry heat destroys bacteria and viruses by very slow oxidation (burning) and is even slower as a sterilizing agent than moist heat. In 6 hours at 250° F., 3 hours at 285° F. and 1 hour at 340° F., dry heat will distribute by convection at atmospheric pressure to all inoculum on an oven's contents, including B. stearothermopolis endospores. Dry heat furnaces are typically operated for 2 hours at 320° F. to sterilize. While higher dry heat temperatures can shorten the sterilization time, the risk of heat damage to the materials being sterilized increases proportionately.

Ethylene oxide, an alkylating agent, sterilizes even more slowly than dry heat. After several hours of treatment, often overnight, the sporicidal chemical ethylene oxide (gas) sometimes under pressure and/or at slightly elevated temperatures (120° to 140° F.), will distribute to all inoculum on a chamber's contents, including B. stearothermopolis endospores.

The extended times required for moist heat, dry heat and ethylene oxide sterilization burden the economy. Surgical tools are removed from use for long periods while being sterilized, and capital outlay for such tools is, therefore, not ideal. Accordingly, sterilization by any of these methods is near economically impractical where rotating operatories are used, such as in dental offices.

Moreover, no single one of these methods is suited to sterilize all of the sundry tools and materials used in medical practice.

Moist heat causes rubber gloves to rapidly loose tensile strength. The loss is grossly noticeable after as few as 4 autoclave cycles. Undetected ruptures in these barriers to infection can have catastrophic consequences. Moist heat sterilization rapidly corrodes metal instruments and dulls blades. Moist heat destroys the connecting resins in fiber optics. Noticeable reduction in light transmitted through a dental handpiece's fiber optic light orifices occurs after just a few autoclave cycles. Moist heat can damage plastics. Moist heat is unsuitable for sterilizing anhydrous oils, greases, lubricating jellies and powders. Many surgical instruments, like dental drill handpieces and scopes, contain not only metal, but, also plastic, rubber and resin parts and oils and greases. Also, lubricating jellies in the case of scopes.

Dry heat will sterilize powders only after impractically long exposure and is also entirely unsuited for sterilizing greases, lubricating jellies and anhydrous oils. Further, dry heat is entirely unsuited for fabrics, plastics and rubber goods. Dry heat also destroys metal and solder joints and dulls blades. Dry heat destroys the temper of metal instruments. Most commercial solders actually metal at about 450° F. Carbon steel instruments are heat treated for hardness and should not be routinely sterilized at temperatures about 325° F.

Ethylene oxide ($C_2H_4O$) (normally mixed with $CO_2$ or gases to reduce explosion hazard) can sterilize many heat sensitive items without damaging them. However, sterilizing with ethylene oxide has its own unique set of problems. Ethylene oxide, a derivative of petroleum hydrocarbons and a flammable carcinogen, presents what are, unacceptable risk for both health care workers and their patients, including risk of explosion. Ethylene oxide sterilizers are also large, cumbersome, difficult to use and prohibitively expensive outside of the hospital environment. Additionally, ethylene oxide takes even longer, substantially longer, to sterilize than both moist and dry heat sterilization, which, each, themselves, already takes an undesirably long time to sterilize. Exposures to treatment with ethylene oxide for at least several hours and, often overnight are required. Significant additional time is also needed to dissipate residuals of this hazardous chemical from sterilized materials that have absorbed it. Hazardous quantities of ethylene oxide persist in plastics, rubbers and fabrics for several hours, even for days, following treatment. 128 hours after a 16 hour treatment with ethylene oxide, leather was found to have still retained 10 percent to 18 percent of the absorbed gas.

The need to manufacture so many different types of apparatus to sterilize all of the diverse tools and materials used in medical practice creates at least inefficiencies of scale which burden the economy.

Ozonators or ozonizers, which have been employed for over a century to sanitize, have also recently been employed to sterilize with limited success. Ozonators are used extensively in Europe for the treatment of municipal drinking water supplies and in the U.S. for the treatment of sewage gases. The allure of using ozone ($O_3$) to sterilize is that this single method could, potentially, rapidly sterilize all of the sundry tools and materials used in medical treatment without damage.

Ozone, that is triatomic oxygen ($O_3$), is highly reactive. On contact, this strong oxidant reacts with the hydrophobic fatty acid tails of the phospholipids, which form the phospholipid bilayer of bacterial cell membranes. This chemical reaction cleaves the double bonds in these unsaturated fatty acids. This, in turn, alters cell permeability, thus, lysing the cells, and thereby, achieving a bactericidal effect. $O_3$ also cleaves the double bonds in the functional groups of the polypeptide chains forming the protein capsids of viruses, thus, also compromising these barriers and, thereby, achieving a biocidal effect. $O_3$ is proved to kill on contact pathogenic bacteria of the genuses *Escherichia* (meningitis), *Salmonellas* (typhoid fever), *Legionella* (Legionnaire's disease), *Streptococcus* (bacterial pneumonia, septicemia, endocarditis, scarlet fever, *Vibrio* (cholera), influenza viruses, polio viruses, various fungi and other parasites, like the amoebas and other protozoans and their cysts (malaria, sleeping sickness), including crypto sporidium. $O_3$ is known to kill parasites as large as nematodes or round worms, including enterobius vermicularis (pin worms) and *Trichinella spiralis* (trichinosis). $O_3$ eliminates pathogenic bacteria and viruses from 3, 125 times more rapidly than Cl (chlorine). Moreover, unlike Cl, $O_3$ does not leave carcinogenic residues that impart a characteristically unpleasant taste and odor to the water.

Both $O_3$ and O have oxidizing potentials which are each, themselves, greater than the oxidizing potential of hypochlorous acid, a bleaching and chlorinating agent and disinfectant, which, itself, is recognized as a very strong oxidizing agent. The very germicidal power of Cl (chlorine) is dependent upon the release of free hypochlorous acid. Yet, the oxidizing potential of HC10 is only 1.36 V. The oxidizing potential of O is 2.07 V. The oxidizing potential of $O_3$ is 1.67 V. $O_3$, second only to F (fluorine) and O in electronegative oxidation potential, with F being the most electronegative of the elements on the Pauling Scale.

The stainless steels used to fabricate surgical instruments are very resistant to $O_3$ breakdown. Unlike moist heat and some germicidal solutions, $O_3$ is unlikely to either disturb or prevent the formation and/or repair of the chromium oxide layers, that is oxide films, which provide strong resistance to corrosion of these high carbon steels. Like ethylene oxide, $O_3$ can safely sterilize heat sensitive materials. Ozone treatment is most effectively accomplished at temperatures below 100° C. Ozonators need not be operated at temperatures that might heat damage sensitive materials. Unlike ethylene oxide, $O_3$ leaves no hazardous residues as it rapidly breaks down to the more stable diatomic oxygen molecule $O_2$ in atmosphere. $O_3$ will breakdown and sterilize gums, fat deposits, scums, oils, jellies and soils.

Sanitizing ozonators use one of two methods to produce ozone. Dehumidified air or O under pressure is passed by an ultraviolet lamp or, alternatively, through a glow discharge. Diatomic oxygen ($O_2$), the more suitable molecular form of oxygen, is split into atomic oxygen when bombarded with either electrons or electromagnetic radiation, having energy sufficient to split the O to O double bond of $O_2$, that is 6 eV to 7 eV. The quite highly reactive single atomic oxygens then bond with other $O_2$ molecules to form $O_3$ ($3O_2(g)$+ Energy=$2O_3(g)$). The glow or corona discharge method produces far greater quantities of ozone per volume of O (1-10% ozone by volume) than UV.

A typical corona discharge ozonator consists of two electrically opposed plates, having a tension between 7,000 and 20,000 VAC and separated by a sheet of dialectic. Air or O under pressure (usually 1.2 to 2 atm) is passed between each plate and the dielectric surface. The ozonated air is then, hopefully diffused to remote pathogens and other contaminants.

The basic problem with achieving the sterilization of objects through ozone treatment is no different than the basic problem with achieving sterilization through other antimicrobial agents such as moist heat, dry heat, ethylene oxide or germicidal solutions. The problem is one of distribution. To be a sterilant, as opposed to just a sanitizing or disinfecting agent, an agent must be distributed in lethal quantity to all virulence. No viable population can live upon a sterile object. The highly unstable $O_3$ molecules quickly breakdown in atmosphere to form $O_2$. $O_3$ is subject to unimolecular reaction. An ozone molecule, $O_3$, which is energetically excited by, for example, molecular collision, absorbing a photon, or heating, spontaneously decomposes to dioxygen and atomic oxygen. At room temperature, surface reactions appear most responsible for the decomposition of $O_3$. The half life of the $O_3$ molecule, even in dry atmosphere, is a mere 20 to 100 minutes, normally about 30 minutes, and this short half life is, of course, quite adversely effected by increased temperature and humidity. $O_3$, therefore, cannot be stored, and if $O_3$ is to be employed as anything more than a haphazard sanitizing agent, it must be generated very close to its point of application.

In U.S. patent application Ser. No. 09/939,169 (now U.S. Pat. No. 6,713,027 B2), this inventor teaches of an apparatus and method for sterilizing dental drill handpieces, which are made in large part of metal. These surgical tools are particularly problematic to sterilize by any single of the earlier described methods for sterilizing as they contain not only the metal parts but also rubber and/or plastic gaskets, rings and stoppers, lubricating oils and fiber optics. The handpieces also contain lumens, which are difficult themselves to sterilize and precision moving parts such as bearings, which are damaged if operated while still imperceptibly expanded by heating.

The handpieces are connected as an electrode plate of a corona discharge ozonator operated at $\frac{1}{1,000}$th atmosphere without a solid dielectric separating its two electrically opposed plates. Sufficient AC tension is applied to the plates to produce an abnormal glow discharge about the tools. Of course, the abnormal glow discharge not only covers all metal surfaces of the tool and causes the ion bombardment and UV irradiation thereof, but it also produces very small amounts of ozone at all the metal surfaces and immediately adjacent to all non-metallic parts of the handpieces and their lubricants. Dental drill handpieces were successfully sterilized by this method in 10 minutes or less and with the temperature of the handpieces not exceeding 215° F. throughout the treatment. Before the chamber reopened, off gas was exhausted through a micron (reactive charcoal) filter which is shown on the preferred embodiment.

In U.S. Pat. No. 6,007,770, issued to Peiper et al on Dec. 28, 1999, Peiper teaches that ozone can be generated in a sealed vessel, which contains materials to be sterilized and which, uncharacteristically, may also be a "closed plastic bag". The vessel is placed between the plates of a corona discharge ozonator which, itself, is contained within an chamber. Each plate of the ozonator has a sheet of dielectric placed between it and the vessel or in the alternative, the vessel may act as the dielectric which separates the ozonator's electrically opposed plates. An electrode or electrodes, which are capacitively coupled to one or the other of the plates, may also be contained in the vessel hollow. The vessel and its contents always act in one manner or another as an integral part of the ozonator. When the ozonator is energized, ozone is produced within the vessel hollow.

This Peiper ozonator is a very inefficient ozonator and provides little to no time advantage over prior art sterilizers. A voltage drop occurs across the vessel's insulative glass or plastic walls. The bulk of the ozone is produced between the ozonator plates and the vessel's exterior surfaces and not within the vessel hollow. Placing additional electrodes within the vessel hollow is unlikely to significantly enhance the ozone production therein as such small electrode surfaces cannot charge significantly ($C_{uuF}$ equaling 0.225 K A/S). Moreover, and as noted by Peiper, this arrangement of internal electrode(s) risks damage from arcing discharges to both electrodes and the other materials contained within the hollow. Peiper also does not teach any means for conducting the ozone to the interior surfaces of any lumens or crevices of the materials to be sterilized or through any oils or jellies contained thereon. Ozone transport within the vessel hollow relies upon random molecular collision alone. If the Peiper ozonator would sterilize objects with complicated surfaces, including enclosed interior surfaces, at all, it would likely accomplish this only after long exposure of the objects to ozone treatment. Peiper teaches that his ozonator takes from a minimum of 10 minutes to a maximum of 30 minutes just to sterilize simple plant specimens. This raises a second concern with the Peiper ozonator.

An ozonator's electrode plates, which typically operate at 250 W per cubic foot of electrode plate, are known to rapidly heat to a temperature comparable to the temperature at which autoclaves and/or sterilizing ovens operate. Therefore, with extended ozone treatments, the Peiper ozonator could present the same, if not greater risk, of heat damage to any plastics, rubbers, fabrics or other heat sensitive materials being sterilized as would autoclaves or sterilizing ovens. Moreover, ozone production with the vessel hollow would, itself, be compromised by even moderate heating. Thermal decomposition of $O_3$ has been extensively studied within a range of 80° C.-500° C. $O_3(g)$ rapidly decomposes at temperatures above 100° C. Thus compromised, the ozonator might fail to sterilize entirely. One embodiment of the Peiper ozonator has both an intake fan and a separate exhaust port installed in its chamber walls for cooling its ozonator, but only to lesser degree the contents within the more equally resistant glass or plastic vessel.

This raises a third concern with the Peiper ozonator. It is necessarily large, intricate and an expensive assemblage of discrete parts, and it is unlikely that sterilization can be economically practiced with such an assemblage. The assemblage includes a chamber to protect workers from exposure to the ozonator's high power parts and/or for housing apparatus to cool the ozonator. A free standing ozonator is needed. Means (not shown) for securing the vessel between the ozonator plates is needed. Any electrodes within the bag must be spaced significant distances from each other to prevent undesired arcing discharges.

Finally, Peiper teaches no method for destroying the ozone off gas remaining in the vessel (or the huge concentrations within the chamber) after sterilization. Like ethylene oxide, even in minute quantity, ozone is a noxious gas and known carcinogen and pollutant. Needless to say, it would be risky to regularly expose workers opening the chambers and vessels to retrieve materials and the environment to the concentrations of ozone that would be contained just within each vessel. As ozone has a half life of 20 to 100 minutes in dry atmosphere, the vessels would likely need to sit for hours after treatment before workers could safely open them.

The Peiper ozonator does not appear competitive with prior art methods of sterilization, though the concept of generating ozone within a bag for the purpose of sterilizing objects therein is not entirely without merit.

An inexpensive ozonator, which is capable of rapidly sterilizing all of the sundry items requiring sterilization in the medical industry, at low temperature, is still needed and desirable.

SUMMARY OF THE INVENTION

The present invention improves upon the Peiper sterilizer inventions in U.S. Pat. No. 6,007,770 by teaching means for enhancing the relative volumes of ozone per time interval produced within the sterilization vessel, teaching means for rapidly distributing that ozone to all surfaces of the materials being sterilized within the vessels and through any oils, jellies or soils thereon and teaching means for rapidly destroying the ozone off gas remaining in the vessel after sterilization and before the vessel is opened by workers to retrieve sterilized materials, while maintaining temperatures within the vessel about or below 100° C. throughout the ozone treatment.

The invention consists of a sealed multi-chambered bag, that is a flexible container, which is made of dielectric material and which contains two electrode plates (preferably screen plates) that are separated by an internal wall of the bag. Materials to be sterilized are placed between one or the other or both of the electrode plates and the interior wall. The interior wall allows the ozonator plates to be contained within the bag without the risk of damaging high voltage discharges occurring between plates. The ozonator's optimal ozone production occurs in the bag immediately adjacent to where the materials to be sterilized are located. The bag is placed within a chamber containing an aperture which is connected to the intake of a pump. A conductor and/or semi-conductor connects each electrode plate to an opposed terminal of a high tension transformer. Both the pump and the transformer are connected to timing circuitry, which turns on the pump and the transformer and, then periodically turns the pump off and on to deflate and re-inflate the chambered bag (V is proportional to I/P) and circulates the ozone produced therein to all virulence on the materials being sterilized. The gas within the bag alternatively expands and is then compressed, before turning the transformer off. The timer circuit allows the pump to continue to cycle on and off thereafter (preferably at an increased cycling rate) until the ozone off gas remaining in the bag is destroyed by molecular collision, surface reactions or otherwise. The timing circuitry may be common to both the pump and transformer. The bag may contain some conductive surface areas for the purpose of making connections or for other purpose.

With these enhanced ozone production and circulation features, the ozonator of the present invention sterilizes objects with even complicated interior surfaces constructed of both metal and non-metal materials, and containing lubricants in a treatment cycle of 10 minutes or less, and, therefore, without allowing time for the energized ozonator plates to heat to a point where they might damage any of the objects heat sensitive parts. No appreciable pernicious off gas remains.

For purposes of the present disclosure, the terms "ozonizer" and "ozonator" are used interchangeably.

BRIEF DESCRIPTION OF THE DRAWINGS

The various embodiments, features and advances of the present invention will be understood more completely hereinafter as a result of a detailed description thereof in which reference will be made to the following drawings.

DETAILED DESCRIPTION OF A PREFERRED EMBODIMENT

Figure 1:
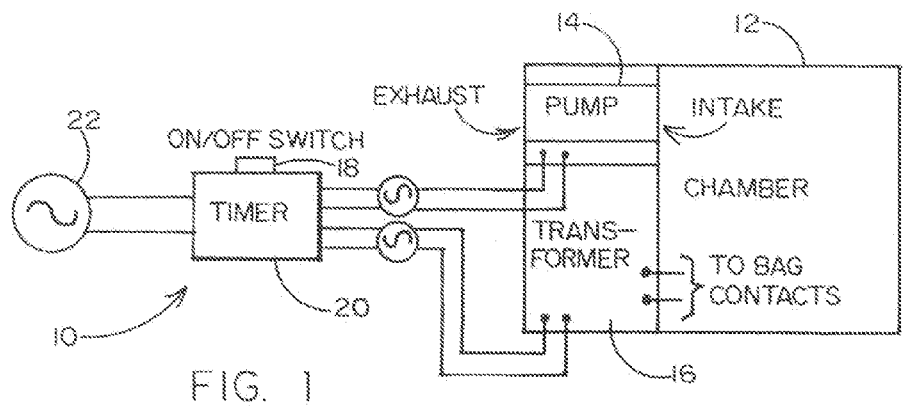
FIG. 1 is a schematic diagram of an ozonizer bag-shaped apparatus according to a preferred embodiment of the present invention.

Referring to the accompanying figures and initially to FIG. 1, it will be seen that an ozonizer apparatus 10 in accordance with a preferred embodiment of the present invention comprises a chamber 12 connected through an intake to a pump 14 and also connected to a transformer 16. The pump and transformer are connected respectively to an on/off switch 18 and timer 20 which are, in turn, connected to a power source 22 such as an AC wall outlet. Pump 14 is designed to selectively remove air from chamber 12 and designed to provide a high voltage (i.e., 20,000 Volts) low current source to bag electrical contacts located within chamber 12 as will be discussed below.

Figure 2:
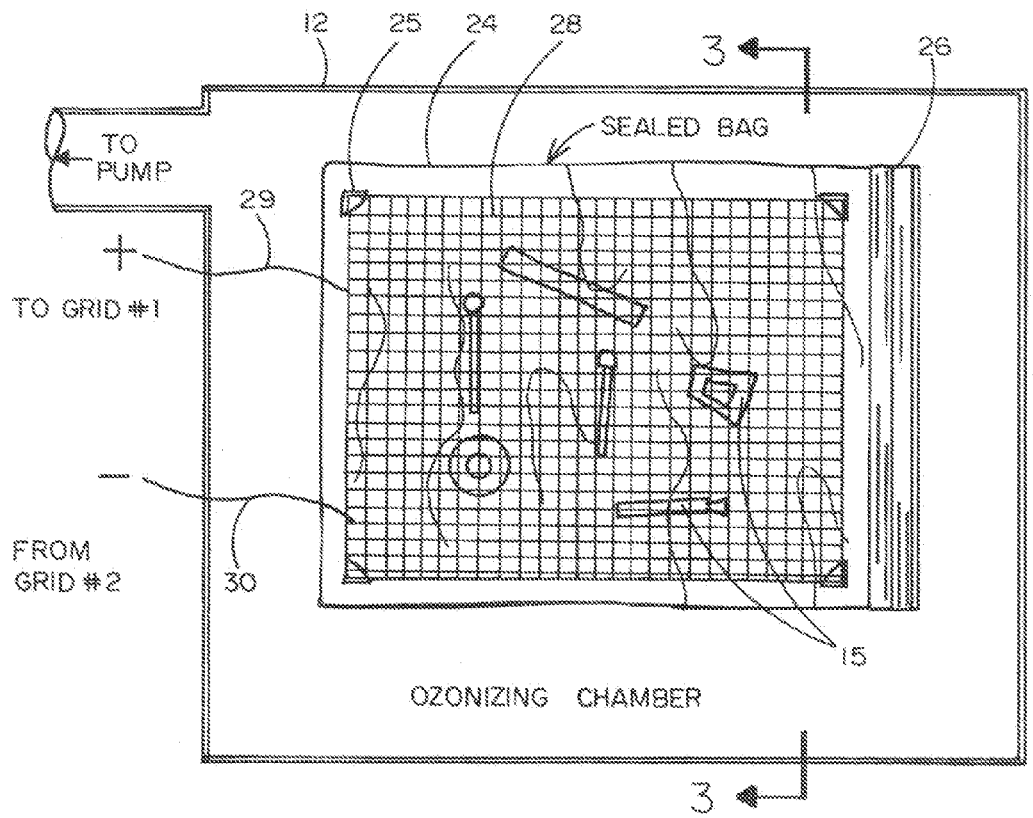
FIG. 2 is a schematic diagram of the chamber and bag of the preferred embodiment.

As shown in FIG. 2, in the preferred embodiment there is positioned within chamber 12 a high temperature plastic bag 24 having a re-sealable opening 26 at one end. It will be seen in FIGS. 3 and 4 that bag 24 has an intermediate dielectric layer 34 which separates the bag interior into two compartments. Each interior side wall of bag 24 has a plurality of holders 25 which secure a grid 32. Nets 28 form side pockets on the side walls of layer 34. Dielectric nets 28 prevent grid 32 from contacting instruments 15. Net 28 may be a perforated sheet of dielectric material. One such grid is connected to one output terminal of transformer 16 by means of a wire 29. The other such grid is connected to the other output terminal of transformer 16 by means of a wire 30 as depicted in FIG. 2. Wires 29 and 30 are fed through respective side wall surfaces of bag 24 in a sealed manner to avoid gas leakage through the sealed bag.

Figure 3:
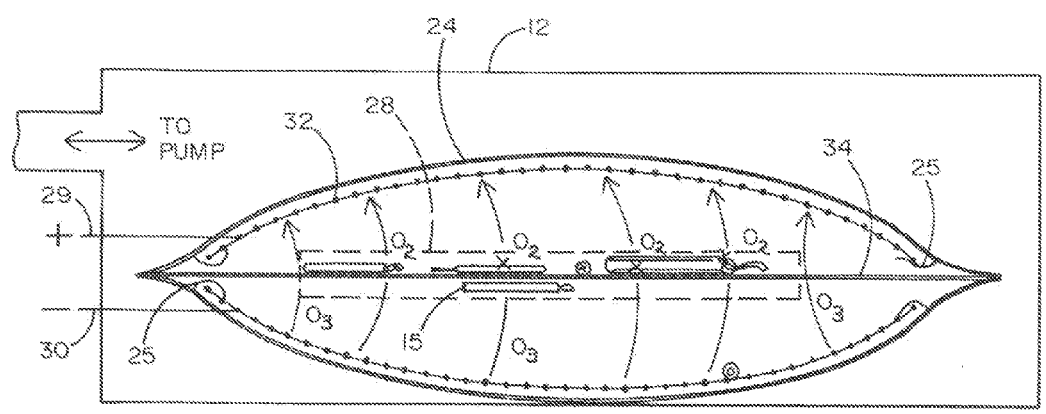
FIG. 3 is a cross-sectional view taken along lines 3-3 of FIG. 2 wherein the bag is shown fully expanded due to reduced pressure within the chamber.
Figure 4:
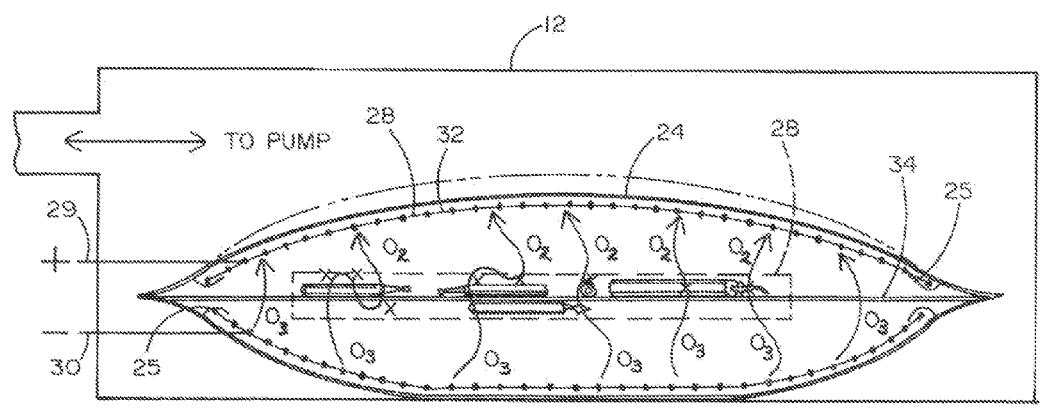
FIG. 4 is a view similar to FIG. 3 but shown with the bag volume partially reduced due to a higher pressure within the chamber.

To operate ozonizer apparatus 10, items 15 to be sterilized are placed inside the bag 24 on both sides of layer 34 between nets 28 and layer 34 with the bag within chamber 12 and in a sealed condition with re-sealable opening 26 securely closed. With on/off switch 18 in the "on" condition, timer 20 is activated and pump 14 begins removing air from the chamber. Sealed bag 24 responds to the decreased pressure in the chamber by expanding. At a pre-determined time after pump activation, transformer 16 is turned on thereby applying ozone-generating voltage to conductive screens 32. FIG. 3 illustrates the condition wherein bag 24 is fully expanded, corresponding to minimum pressure in the chamber. At this point, the timer 20 begins a cycling operation wherein pump 14 is briefly turned off thereby allowing some pressure increase in chamber 12 so that fully expanded bag 24 begins to reduce its volume as shown in FIG. 4. During the majority of the remaining sterilization process, high voltage at grids or screens 32 is maintained while pump 14 is repeatedly turned on and off in sequence thereby periodically altering the bag volume and stimulating the movement and interaction of ozone with items 15 within the bag. After several minutes of such ozone sterilizing of the items with the bag, the timer 20 turns off transformer 16 but continues the pump cycling operation to dissipate the remaining ozone prior to completion of the process. Such dissipation occurs by conversion of ozone into oxygen within the sealed bag so that when the bag is unsealed to remove items 15, little or no ozone remains. Then, the pump is deactivated and the chamber may be opened to gain access to bag 24 and the sterilized items therein.

It will be understood by those having skill in the relevant art that the disclosed ozonizer apparatus and inventive bag used therein, are currently contemplated as the best mode of the invention. However, those having the benefit of the above disclosure will now perceive various modifications and additions which may be made to the underlying invention herein. Therefore, it should also be understood that the scope hereof is not to be limited by the disclosed embodiment, but only by the appended claims and their equivalents.

I claim:

1. An ozonizer apparatus for sterilizing items, the apparatus comprising:
   a chamber containing a sealable non-conductive bag for receiving said items;
   a pump for selectively reducing air pressure within the chamber;
   a high voltage transformer for supplying a high voltage within said chamber;
   said bag having at least two compartments separated by a dielectric material, each such compartment having a conductor connected to said high voltage transformer for generating ozone within said bag; and
   a timer for controlling operation of said pump and of said transformer for causing said ozone to circulate among said items within said bag for a selected period of time.

2. The apparatus recited in claim 1 wherein said conductor in each said compartment of said bag comprises a conductive screen.

3. The apparatus recited in claim 2 wherein each said conductive screen is contained within a pocket formed on an interior side wall of said bag.

4. The apparatus recited in claim 1 wherein said timer is configured for sequentially cycling said pump on and off for causing said bag to alternately inflate and deflate repeatedly.

5. The apparatus recited in claim 1 wherein said bag including said dielectric material is made of a high-temperature-resistant plastic.

* * * * *